(12) United States Patent
Belluzzi

(10) Patent No.: US 11,137,097 B2
(45) Date of Patent: Oct. 5, 2021

(54) REUSABLE SEALING CONNECTOR DEVICE FOR A FLEXIBLE TUBE

(71) Applicant: ASEPTCONN AG, Dietikon (CH)

(72) Inventor: Riccardo Belluzzi, Dietikon (CH)

(73) Assignee: ASEPTCONN AG, Dietikon (CH)

(*) Notice: Subject to any disclaimer, the term of this patent is extended or adjusted under 35 U.S.C. 154(b) by 405 days.

(21) Appl. No.: 16/331,762

(22) PCT Filed: Sep. 12, 2017

(86) PCT No.: PCT/EP2017/072941
§ 371 (c)(1),
(2) Date: Mar. 8, 2019

(87) PCT Pub. No.: WO2018/046771
PCT Pub. Date: Mar. 15, 2018

(65) Prior Publication Data
US 2019/0249808 A1    Aug. 15, 2019

(30) Foreign Application Priority Data
Sep. 12, 2016 (IT) .................. 102016000091809

(51) Int. Cl.
*F16L 33/22* (2006.01)
*A61M 39/12* (2006.01)

(52) U.S. Cl.
CPC ........... *F16L 33/224* (2013.01); *A61M 39/12* (2013.01)

(58) Field of Classification Search
CPC ....... F16L 33/224; F16L 33/22; F16L 33/222; F16L 33/223; F16L 33/225

USPC ............. 285/247, 248, 249, 322, 324
See application file for complete search history.

(56) References Cited

U.S. PATENT DOCUMENTS

| | | | | |
|---|---|---|---|---|
| 2,423,632 A | * | 7/1947 | Ansorge | F16L 33/222 285/249 |
| 3,606,396 A | * | 9/1971 | Prosdocimo et al. | F16L 19/045 285/148.18 |
| 3,980,325 A | * | 9/1976 | Robertson | F16L 19/08 285/249 |
| 4,900,068 A | * | 2/1990 | Law | F16L 33/222 285/139.2 |
| 10,550,969 B2 | * | 2/2020 | Shorrock | F16L 19/0206 |
| 2005/0099004 A1 | * | 5/2005 | Bouey | F16L 33/224 285/249 |
| 2008/0185843 A1 | * | 8/2008 | Roll | F16L 33/224 285/382.2 |
| 2008/0272590 A1 | * | 11/2008 | Howard | F16L 33/224 285/247 |

(Continued)

FOREIGN PATENT DOCUMENTS

| | | |
|---|---|---|
| DE | 202015106514 U1 | 1/2016 |
| EP | 1841998 B1 | 1/2009 |

(Continued)

*Primary Examiner* — Aaron M Dunwoody
(74) *Attorney, Agent, or Firm* — McGlew and Tuttle, P.C.

(57) ABSTRACT

The reusable sealing connector device for a flexible tube comprises a tubular element (2), a clamping sleeve (3), predisposed to be associated coaxially with said tubular element (2) and a clamping ferrule (4), predisposed to cooperate with the clamping sleeve (3) for clamping the flexible tube inserted on the tubular element (2), internally to said clamping sleeve (3).

18 Claims, 8 Drawing Sheets

(56) References Cited

U.S. PATENT DOCUMENTS

2010/0156095 A1\* 6/2010 Inoue .................... F16L 33/224
                                                        285/249
2014/0246853 A1\* 9/2014 Bucchi ................. F16L 33/222
                                                        285/343
2020/0378537 A1\* 12/2020 Firmian ............... F16L 33/222

FOREIGN PATENT DOCUMENTS

| EP | 2233814 A1 | 9/2010 |
| FR | 2 640 720 A1 | 6/1990 |
| WO | 98/01695 A1 | 1/1998 |

\* cited by examiner

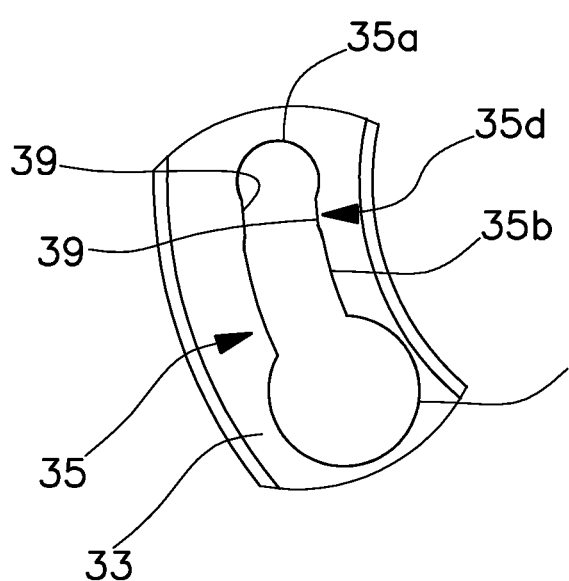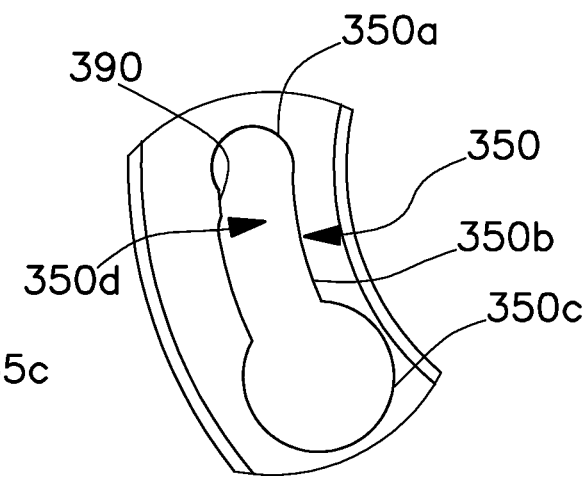
Fig.10　　　　　　　Fig.11
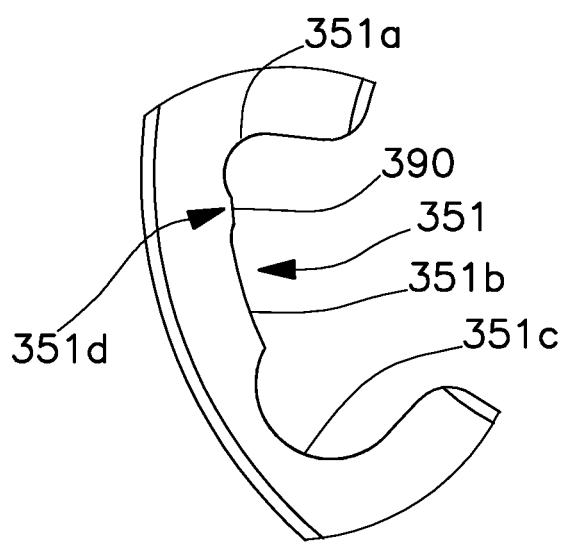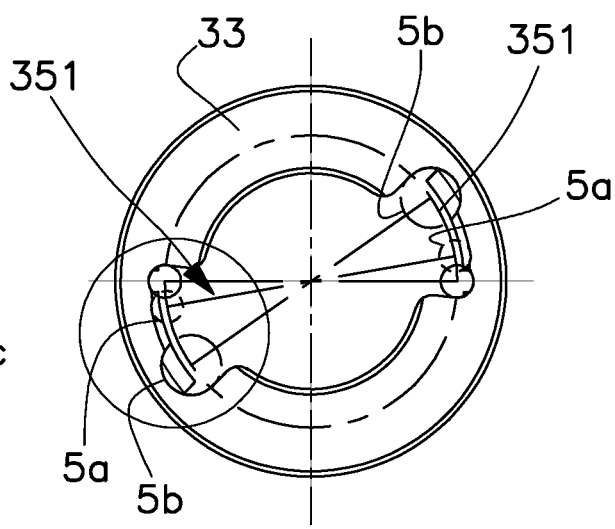
Fig.12　　　　　　　Fig.13

REUSABLE SEALING CONNECTOR DEVICE FOR A FLEXIBLE TUBE

TECHNICAL FIELD

The present invention concerns a reusable sealing connector device for a flexible tube.

BACKGROUND ART

Reusable connector devices for flexible tubes are known, in particular used in the medical field, for connecting medical apparatuses by flexible tubes for supplying or dispensing a liquid, preferably made of material of the type of silicone.

Connector devices used in such field, in particular, require a complete sterility, further to the possibility of being easily reused, for example for allowing the substitution of flexible tubes.

EP 1841998 discloses, for example, a connector sealing device for liquids, for connecting a flexible tube, comprising a tubular element for insertion of the flexible tube, a clamping sleeve provided with at least two segments distributed along the circumference of the sleeve, which protrude from the tubular element and are externally provided with a stopping inclined surface, and a coupling nut cooperating with the said stopping inclined surface of the segments of the clamping sleeve, through an internal stopping inclined surface, so as to compress the same elements against the flexible tube.

Such solution, as well as others of known type, presents some disadvantages, as it does not allow an easy disassembling of the three elements constituting the connector device. In particular, the solution disclosed in EP 1841998 provides a threaded connection between the coupling nut, generally made of metallic material, and the clamping sleeve, made, instead, of plastic material. It is to be observed, for example, that during the disassembly operations, necessary for reusing the connection, such threaded coupling between different materials presents a risk of slipping, as well as of deterioration of the thread of plastic material.

EP 2233814 discloses a disengageable connector device for connection with a tube, in particular of the quick-connection type, comprising a main body and a clamping element, for the disengageable connection of the tube. The main body comprises a nipple, on which the tube can be inserted, and the nipple has a portion spaced from the cylindrical form on the respective external surface, on which the tube is sealingly fixed by the clamping element.

WO 98/01695 discloses a connector device for tubes of synthetic resin, comprising a main body for inserting the tube, which has an inserting groove, as well as a series of convex and concave rings obtained on the external circumference of a tube-shaped support of the tube, protruding inside the said groove.

US 2010/0156095 discloses a connector device for a tube, comprising a nipple, a sleeve, a free fixing portion rotatably mounted on an external peripheral surface of the nipple, and also a fixing member to be screwed on an external peripheral surface of the free fixing element so as to be mobile in axial direction towards the sleeve. The free fixing portion and the sleeve are associated in an independent way, so as to be fixed in axial direction.

DE 202015106514 discloses a device for connecting with a tube, comprising a connecting portion, a sleeve and a clamping ferrule that, in an assembled condition, surrounds at least partially the sleeve, and cooperates with it in such a way that when rotating the clamping ferrule into a direction the sleeve sealingly connects the tube with the connecting portion. The sleeve also comprises a fixing portion and a support portion arranged next to the fixing portion that is provided with a stopping radial protrusion towards the interior, predisposed to cooperate with a stopping protrusion of the connection portion for the axial locking.

Nevertheless, such solutions have certain disadvantages, in particular for the difficulty of mounting and dismantling the same device, as well as the tubes to be connected, and/or for the accessibility, thus the cleanliness, of the different components.

Thus, the known solutions for reusable sealing connector devices for flexible tubes, in particular for medical use, do not satisfy completely the necessities of the specific field.

DISCLOSURE

The task of the present invention is to solve the above-mentioned problems, devising a reusable connector sealing device for a flexible tube that allows having an optimal functioning, in particular facilitating both the connecting operations and the detaching operations, in situ.

A further scope of the present invention is that of providing a reusable sealing connector device of simple constructive and functional conception, provided with surely reliable functioning, versatile use as well as relatively economic cost.

The cited scopes are reached, according to the present invention, by the reusable sealing connector device for a flexible tube according to the claim 1.

The reusable sealing connector device for a flexible tube, according to the invention, comprises a tubular element on which an end portion of the said flexible tube is predisposed to be inserted along a longitudinal axis of the same tubular element. The connector device also comprises a clamping sleeve predisposed to be axially inserted around the said tubular element and provided with a connecting end divided into at least a pair of clamping segments predisposed to engage, in a flexible manner, the portion of the flexible tube inserted on the tubular element. Further, the device comprises a clamping ferrule provided with an operating portion predisposed to be inserted around the clamping sleeve for compressing the said clamping segments against the same inserted portion of the flexible tube.

According to a feature of the invention, the device allows to lock the clamping sleeve to the tubular element, in a pre-assembling step. In practice, the two components are reciprocally constrained, both with respect to the rotation and with respect to the axial translation.

According to the invention, the tubular element comprises an annular locking seat obtained around its longitudinal axis, while the clamping sleeve comprises an end locking portion predisposed to be inserted axially into the locking seat and to be locked through locking means.

The annular locking seat preferably has a grooved shape.

According to a particular aspect of the invention, the locking means can shape at least one locking element, preferable at least a pair, inserted in a respective locking hole obtained, for example, on the bottom of the said annular locking seat and through a respective opening obtained on the end locking portion of the clamping sleeve.

More precisely, each opening is configured to be aligned at least partially, in assembled condition, to the at least one locking hole provided for locking the axial translation and rotation of the said locking portion of the clamping sleeve inside the annular locking seat of the tubular element by interposing at least one locking element inserted through the opening and secured in the at least one locking hole.

Preferably such locking elements are of the type of screws and the respective locking holes are threaded holes.

As an alternative, such locking elements are connecting pins, inserted by interference fit, into respective locking holes, not threaded, obtained in the said annular locking seat.

Preferably, the locking elements according to the invention are advantageously locked to the clamping sleeve through a bayonet coupling for permitting, in particular, an easy disassembly of the sole sleeve. In such case, the said passage openings of the locking elements are preferably slot-shaped or shaped differently with a closed or open profile, provided that they are suitable for the purpose. However, the bayonet coupling according to the invention allows both a quick assembly and a quick disassembly of the clamping sleeve from the tubular element, for example for carrying out maintenance, cleaning or substitution operations. As a matter of fact, in both cases, a simple relative movement is sufficient, in particular a relative rotation, between the sleeve and the tubular element, for locking and unlocking the connection between the two said components.

According to a particular aspect of the invention, the cited openings obtained on the end locking portion of the clamping sleeve for the passage of the locking elements comprise an insert portion having a transverse size suitable for inserting a head of a said locking element, a sliding portion having a curved profile for permitting the relative rotation of the clamping sleeve when the said head is inserted, and a fixing portion having a transverse size substantially corresponding to a stem of the said locking element. The same opening also comprises a narrowed portion, interposed between the said sliding portion and the said fixing portion, having a reduced transverse size with respect to the transverse size of the said stem of the locking element. Advantageously the sleeve can be made of elastic material, thus it is possible to snap lock the head of each locking element at the fixing portion of the respective shaped opening. In particular, the snap lock can be obtained through the presence of at least one locking tooth along the internal profile of the cited opening predisposed to engage the stem of the locking element, preventing its movement along the same opening.

Preferably, the cited opening comprises a pair of teeth, facing each other and interposed at the said narrowed portion between the fixing portion and the sliding portion.

The opening obtained in the locking portion of the sleeve can have a slot shape, with closed or open profile, at a rim of the locking portion. In such case, in particular, the profile of the opening preferably comprises, for locking the locking element, one single tooth protruding in way suitable for locking or unlocking the same locking element.

In addition, according to a particular aspect of the invention, the tubular element is directly screwed to the clamping ferrule so that the latter compresses the clamping segments on the flexible tube for a secure connection.

More precisely, to this aim, according to the invention, the tubular element comprises a clamping portion provided with an external threaded surface, while the clamping ferrule comprises an internally threaded coupling portion.

In substance, the tubular element and the clamping ferrule can be firmly constrained, in a disengageable way, thanks to the previously cited locking means, while the threaded coupling between the tubular element and the clamping ferrule allows a quick, and easily dismountable, clamping of the flexible tube. For disconnecting the flexible tube, for instance for its substitution, it is sufficient to unscrew the clamping ferrule while the clamping sleeve and the tubular element can remain reciprocally locked thanks to the said locking means.

According to a particular aspect of the invention, the threaded coupling between the clamping ferrule and the tubular element is realised through a thread of "large" pitch preferably of DIN 405 or DIN 20400 type. The size of the said thread allows an easy and complete access to the cavities that shape the same thread, permitting the integral cleaning of the connector device.

Such provision has the advantage of allowing a fast unscrewing, even independently.

In addition, such provision delays the deterioration of the thread, in particular in case one of the two components, i.e. the ferrule or the tubular element, is made of plastic and the other one is made of steel, or they are both made of plastic.

BRIEF DESCRIPTION OF THE DRAWINGS

Details of the invention shall be more apparent from the detailed description of a preferred embodiment of the reusable connector sealing device for a flexible tube according to the invention, illustrated for indicative purposes in the attached drawings, wherein:

FIG. 10 shows a plant view, enlarged, of a detail of the said second component shown in FIG. 7;

FIG. 11 shows a plant enlarged view of a detail of the cited second component of the connector device, according to a further embodiment;

FIGS. 12 and 13 show respectively a plant enlarged view of a detail and a plant view of the cited second component of the connector device, according to a third embodiment.

BEST MODE

With particular reference to such figures, the reusable sealing connector device for a flexible tube according to the invention has been indicated in its entirety with 1.

In particular, the connector device 1 is for liquid sealing, for connecting a reusable flexible tube, for example of the type employed for medical, pharmaceutical or biotech use, of silicone, PFA or PTFE, for feeding or dispensing such a liquid.

Figure 1:
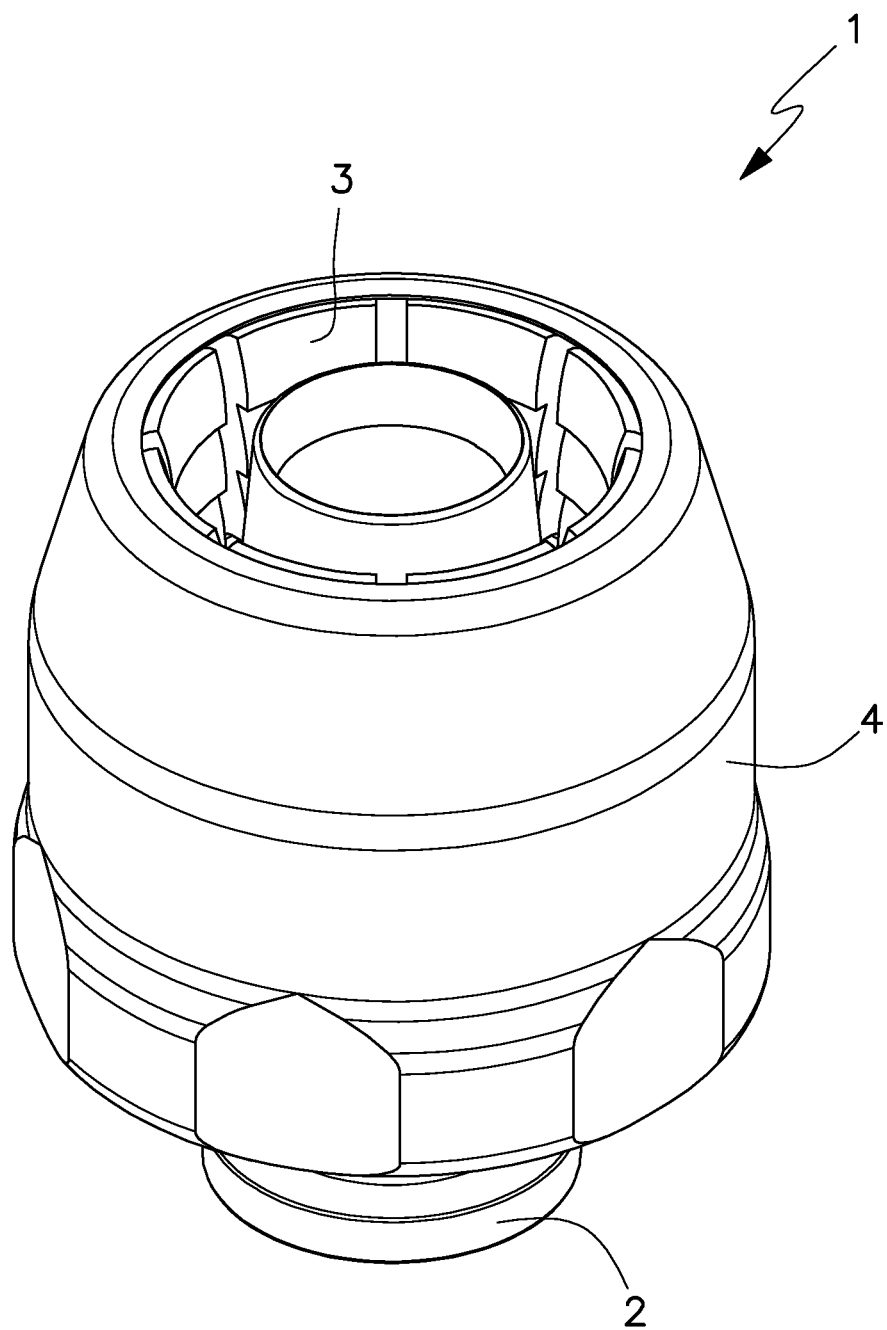
FIGS. 1 and 2 respectively show a perspective view and a plant view of the connector device according to the invention.

The connector device 1 substantially comprises a fitting tubular element 2, a clamping sleeve 3 and a clamping ferrule 4 cooperating for connecting a flexible tube, for example, for the feeding of a medical device (see FIG. 1).

The fitting tubular element 2 is preferably made of material suitable for contact with liquids, for example with aqueous solutions, and is also suitable for being sterile and/or sterilizable. The fitting tubular element 2 is made of, for example, metallic material, preferably of stainless steel.

The tubular element 2 comprises a connecting portion 21 for connection with the flexible tube to be connected, an attachment portion 22, for example, to the medical apparatus, and a clamping portion 23 to the clamping ferrule 4.

The tubular element 2 internally has a tubular cavity, about a longitudinal axis A, predisposed to allow the passage of the liquid to be dispensed.

The connecting portion 21, in particular, externally has a tapered end 21a, suitable for inserting a respective end of the flexible tube to be connected. In practice, this tapered end 21a has a defined conicity, with a diameter decreasing towards the end edge, so as to engage gradually and securely the flexible tube to be connected. The tapered end 21a is fitted to a cylindrical portion 21c, preferably through a shoulder 21b resulting from a slight reduction of the outer diameter.

The connecting portion 21 may also internally have a flared opening 21d at the open end.

The attachment portion 22 is disposed at the opposite end with respect to the connecting portion 21, to allow a secure connection, with an apparatus or for other use. The attachment portion 22 thus preferably has a cylindrical portion 22a connected with a flanged end 22b.

In order to ensure an optimal seal, the attachment portion 22 may have a circular recess 22d, at a joining surface 22c of the flanged end 22b, predisposed to be a seat for suitable sealing means, for example a sealing ring of known type. The attachment portion 22 may also have a profile suitable for the joining of the tubular element 2 with an external component by butt welding.

The clamping portion 23 is arranged between the connecting portion 21 and the attachment portion 22 and shapes a collar 24 protruding with respect to the above-mentioned end portions, thus of greater outer diameter. The clamping portion 23 externally has clamping means to the clamping ferrule 4, preferably of the type of a threaded surface 23a, predisposed for a threaded coupling with a respective inner surface of the clamping ferrule 4, as described in detail below.

The tubular element 2 also comprises a locking seat 25, predisposed to house and steadily lock an end portion of the clamping sleeve 3.

More specifically, the locking seat 25 is shaped by an annular groove 26, coaxial to the tubular element 2, having a depth such as to allow the insertion of a respective end locking portion 31 of the clamping sleeve 3.

Preferably, the locking seat 25 may further comprise at least one clamping hole 27, preferably a pair or more clamping holes 27, for example three, to allow the insertion of as many clamping elements 5, predisposed to mutually lock, in secure manner, the tubular element 2 and the clamping sleeve 3.

Figure 4:
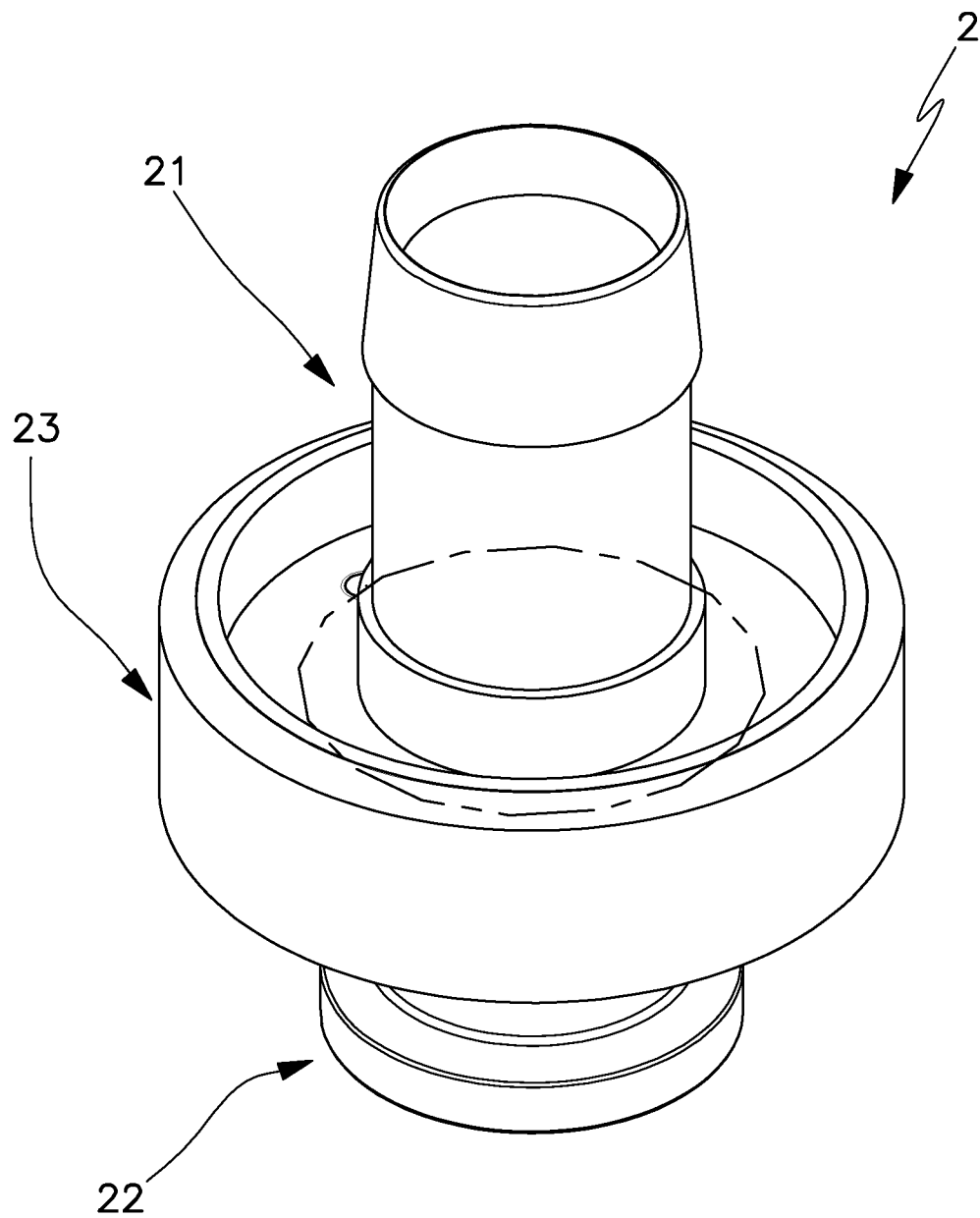
FIGS. 4 and 5 respectively show a perspective view and cross-sectional view according to a longitudinal median plane of a component of the device shown in FIGS. 1 to 3.
Figure 5:
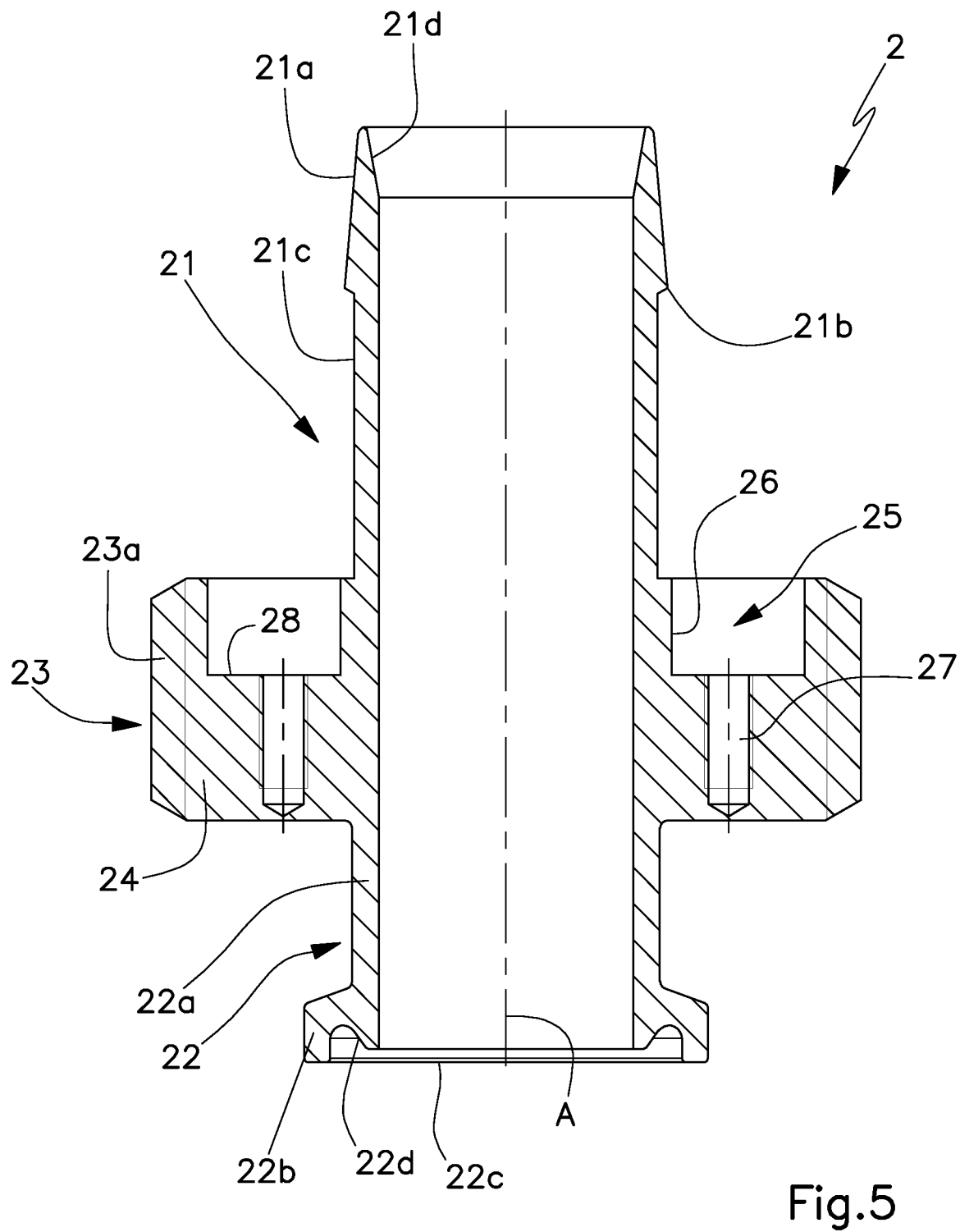

In this case, the locking holes 27 are obtained in the direction of the longitudinal axis A at the annular bottom of the locking seat 25, for example in a diametrically opposite position or, in the case of a plurality of holes, in a number different from two, angularly distributed at the annular bottom 28, about said longitudinal axis A, to ensure a uniform stability of the clamping (see FIGS. 4 and 5). In assembled condition of the connector device 1, said bottom 28 preferably extends on a plane substantially orthogonal to the longitudinal axis A.

The locking holes 27 are preferably threaded and suitable for a locking by threaded coupling with the locking elements 5.

The clamping sleeve 3 is made of flexible material, preferably of plastic, so as to allow a detachable clamp to the tubular element 2.

The clamping sleeve 3 comprises, in addition to said end locking portion 31, an opposite connecting end 32, having a tapered outer surface, intended for clamping around the tube to be connected.

The locking portion 31 externally has, in particular, a conjugate shape, in particular cylindrical, with the shape, also preferably cylindrical, of the locking seat 25 obtained in the tubular element 2, in order to allow the respective clamping inside the same seat 25.

Preferably, the locking portion 31 shapes an annular disc 33 from which a tubular stem 34 extends, for connection with the aforementioned connecting end 32.

The annular disc 33 may comprise one or more locking openings 35, preferably a pair, shaped so as to allow the insertion of said locking elements 5, for a reciprocal locking, easily disengageable or detachable, between the clamping sleeve 3 and the tubular element 2, as described later in detail.

To ensure the stability of the lock and, at the same time, reduce the disassembly times, the locking openings 35 can be configured so as to allow a stable but disengageable, i.e. removable bayonet lock.

The openings 35 may have, for example, an open or closed profile.

Figure 7:
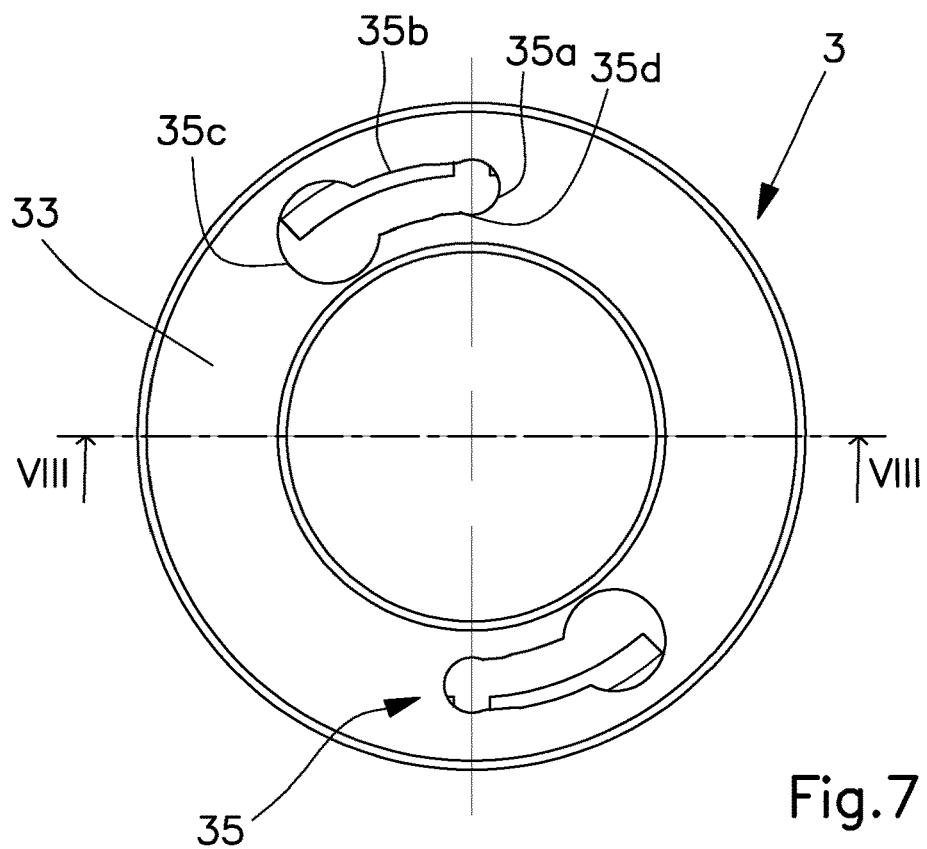

For example, in the case shown in FIGS. 7 and 10, the openings 35 preferably have a slot shape and include, in addition to a fixing portion 35a of transverse size or diameter substantially corresponding to the stem 5a locking element 5, a sliding portion 35b, an insertion portion 35c, having a transverse dimension or diameter greater than the fixing opening 35a, however, in such a way as to allow the insertion of a head 5b of a locking element 5.

Each shaped opening 35 also comprises, advantageously, a narrowed portion 35d interposed between the sliding portion 35b and the fixing portion 35a, of width smaller than the transverse size of the stem 5a of a locking element 5, to ensure an optimal and steady coupling of the locking element 5 at the adjacent fixing portion 35a. In practice, the narrowed portion 35d allows a "snap" insertion of the stem 5a of the locking element 5 in the fixing portion 35a, preventing any accidental release, but at the same time allowing a deliberate release, thanks to the elasticity of the material constituting the sleeve 3.

More precisely, as shown in FIG. 10, the narrowed portion 35d is obtained in the opening 35 through a pair of teeth 39, protruding internally from the profile of the opening 35 and facing each other so as to produce the desired narrowing degree, sufficient to permanently lock the locking element 5 in the fixing portion 35a. The degree of narrowing is preferably in the order of a few tenths of a millimetre.

The presence of the teeth 39 represents an obstacle to the free sliding of the stem 5a of the locking element 5 inside the locking opening 35. More specifically, each tooth 39 blocks the free passage of the locking element 5 from the sliding portion 35b to the fixing portion 35a. The sleeve 3 is advantageously made of elastic material, therefore, by rotating the sleeve 3 with respect to the tubular element 2, as described in detail below, the tooth 39 may be elastically deformed in order to force the insertion, in the event of lockage, or the disengagement, in the event of disengagement, of the stem 5a of the locking element 5 fixed to the tubular element 2 in the fixing portion 35a. Once this fixing portion 35a is reached, the same tooth 39 returns to the non-deformed configuration, thus again constituting an obstacle to the free return of the locking element 5 in the sliding portion 35b. Therefore, thanks to the presence of the teeth 39, the sleeve 3 and the tubular element 2 are securely locked both in axial and rotational direction by means of the locking elements 5.

In particular, in order to unlock the sleeve 3 from the tubular element 2, it is sufficient to force the locking element 5 into the sliding portion 35b by rotating the two components concerned in a relative manner and by elastically deforming the teeth 39, smoothly and quickly, until the head 5b of the locking element 5 reaches the insertion portion 35c. In such position, the sleeve 3 is no longer axially locked and can therefore be easily disengaged in axial direction from the tubular element 2.

As an alternative to the described pair of teeth 39, it is possible to provide that the shaped opening 350 includes only one tooth 390, preferably extending such as to achieve a reduction of the narrowed portion 350d suitable for securing the locking of the locking element 5 in the fixing portion 350a. For example, such an extension can be dimensioned equal to twice the extension of a single tooth 39 if they are a pair, as in the embodiment previously illustrated. The presence of a single tooth 390 correspondingly reduces the processing costs and facilitates, for precision reasons, the realization of the inner profile of the opening 350, requiring a tooth 390 more protruding inwardly (see FIG. 11).

The remaining portions, the sliding portion 350b and the insertion portion 350c, respectively, perform the same function as described above.

Moreover, the opening 351 may alternatively provide a shaped open profile on the rim of the annular disc 33 and hence a single tooth 390, interposed between the sliding portion 351b and the fixing portion 351a, at the narrowed portion 351d. In this embodiment, illustrated in FIGS. 12 and 13, also the profile of the insertion portion 351c of the opening 351 is open and, like the remaining portions, is obtained on the inner rim of the disc 33. This solution is particularly easy and economical by a constructive point of view.

The bayonet coupling, that can be realized for example through the three described variants, advantageously allows reducing the time for mounting and disassembling of the clamping sleeve 3. In fact, as described above, it is sufficient, for example, to perform the relative rotation of the clamping sleeve 3 around the longitudinal axis A, to produce first the release of the locking elements 5 from the fixing portions 35a, 350a, 351a through the narrowed portions 35d, 350d, 351d, and then the passage along the sliding portions 35b, 350b, 351b. When the locking elements 5 are at the insertion portions 35c, 350c, 351c, it is sufficient to make the heads 5b of the locking elements 5 pass through the insertion portions 35c, 350c, 351c to remove the clamping sleeve 3. In particular, disassembly of the clamping sleeve 3 does not require removal of the locking elements 5, for example, by unscrewing: such elements may remain attached to the respective locking holes 27, already provided for example for locking a new clamping sleeve 3, with a clear time saving. In addition, to disengage the clamping sleeve 3, it is sufficient to perform a rotation of the clamping sleeve 3 itself, of a very slight angular width, hence fast to be executed, corresponding to the angular width between the fixing portion 35a, 350a, 351a and the insertion portion 35c, 350c, 351c. As a result, the time involved is in the order of a fraction of a second.

The locking elements 5 are preferably made up of fixing screws provided with hollow head, for example hexagonal (see FIG. 3), to ease the insertion into and the coupling with the locking holes 27. The easy insertion and removal also ensure an access to every part of the component, and therefore a complete cleaning of the same.

Preferably, the connecting end 32 is subdivided into a plurality of clamping segments 36, at least in a pair, by longitudinal notches 37 extending longitudinally, substantially for the whole connecting end 32. The presence of the longitudinal notches 37 enables the same end to be clamped, in a flexible manner, around the flexible tube to be connected, which is in turn predisposed to be inserted around the connecting portion 21 of the tubular element 2 and clamped inside of the clamping sleeve 3.

Figure 6:
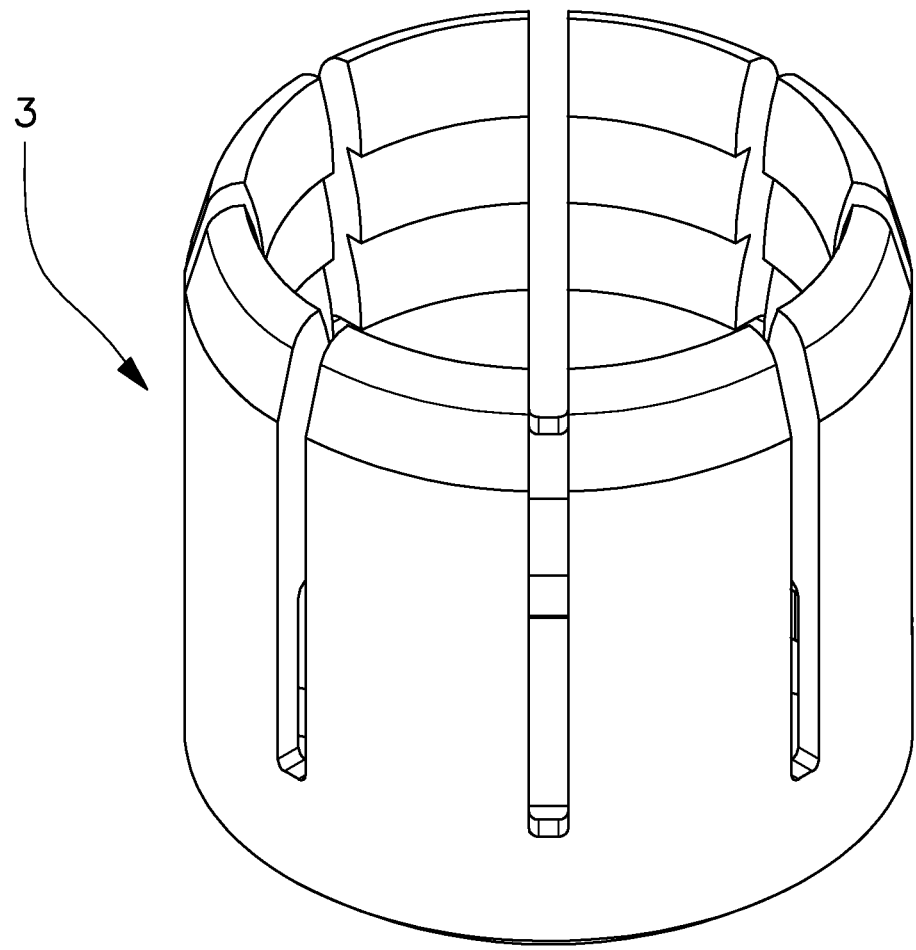
FIGS. 6, 7 and 8 respectively show a perspective, plant and longitudinal cross-sectional view according to the plane VIII-VIII shown in FIG. 7, of a second component of the same connector device.
Figure 8:
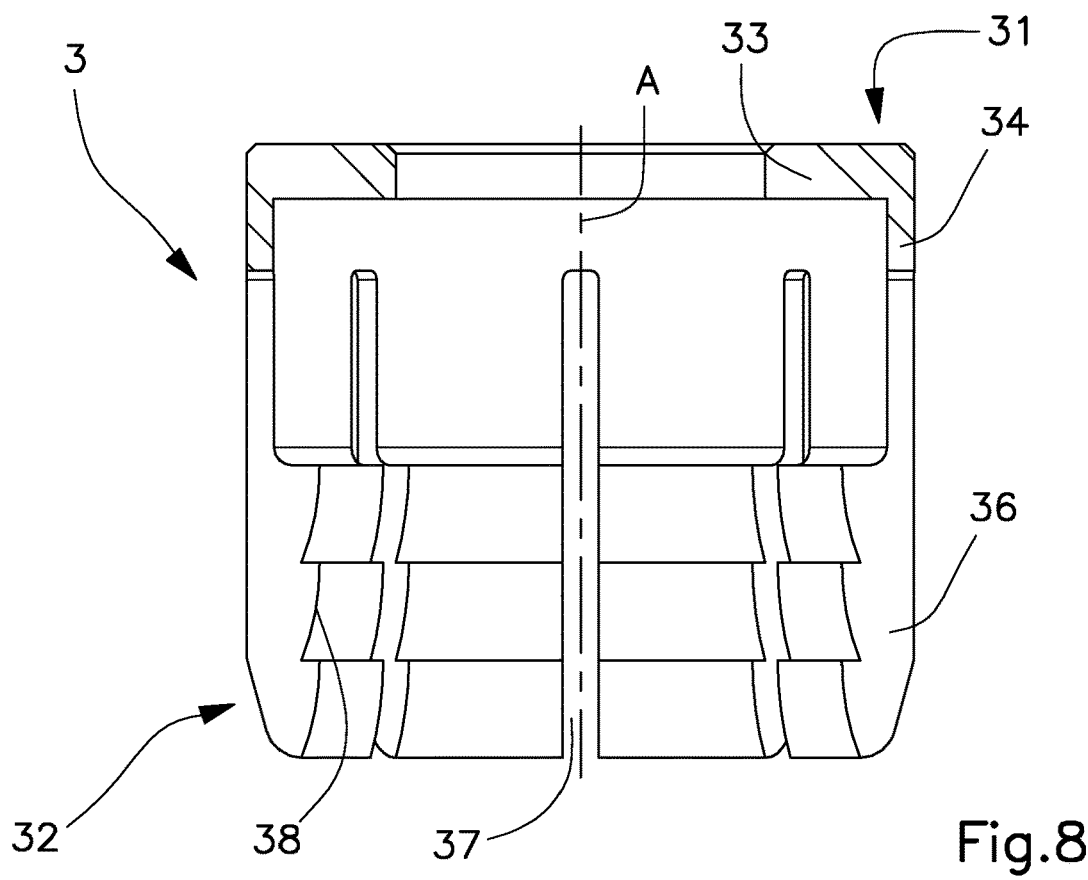

In addition, the clamping segments 36 may internally comprise at least one circumferential groove 38, preferably a plurality of grooves 38 arranged successively (see FIGS. 6 to 8), for an optimum anchoring to the flexible tube to be connected.

Finally, the clamping ferrule 4 comprises a joining portion 41, preferably substantially cylindrical, and an operating portion 42, predisposed to cooperate with the clamping sleeve 3, for clamping the flexible tube to be connected.

In particular, the joining portion 41 internally comprises a coupling portion 43 with the clamping portion 23 of the tubular element 2 preferably threaded.

In particular, the coupling portion 43 can advantageously shape a threaded portion of the DIN 405 or DIN 20400 type. Such kind of thread allows a faster screwing and unscrewing, since it has a so-called "big" thread pitch. In addition, the width of the cavities and protuberances constituting the above-mentioned thread allows an easier cleaning of this component, avoiding dangerous stagnations or deposits of undesirable substances.

Moreover, the particular configuration of said threads preserves the thread from wear deterioration, especially in the case where the tubular element 2 is made of plastic and the clamping ferrule 4 is made of stainless steel or vice versa, or both of them are made of plastic.

In addition, this particular kind of thread has a so-called "anti-grip" behaviour, such as to avoid gripping of the coupled portions, useful in the case where the clamping ferrule 4 and the tubular element 2 are both of metal, for example of steel stainless. Such advantageous behaviour allows preventing use of expensive wear-resistant materials, like bronze, for example for the clamping ferrule 4. The same joining portion 41 externally has the shape of a nut, comprising a clamping surface 44 suitable for manual clamping or for engagement with a tool like a clamp wrench.

Figure 3:
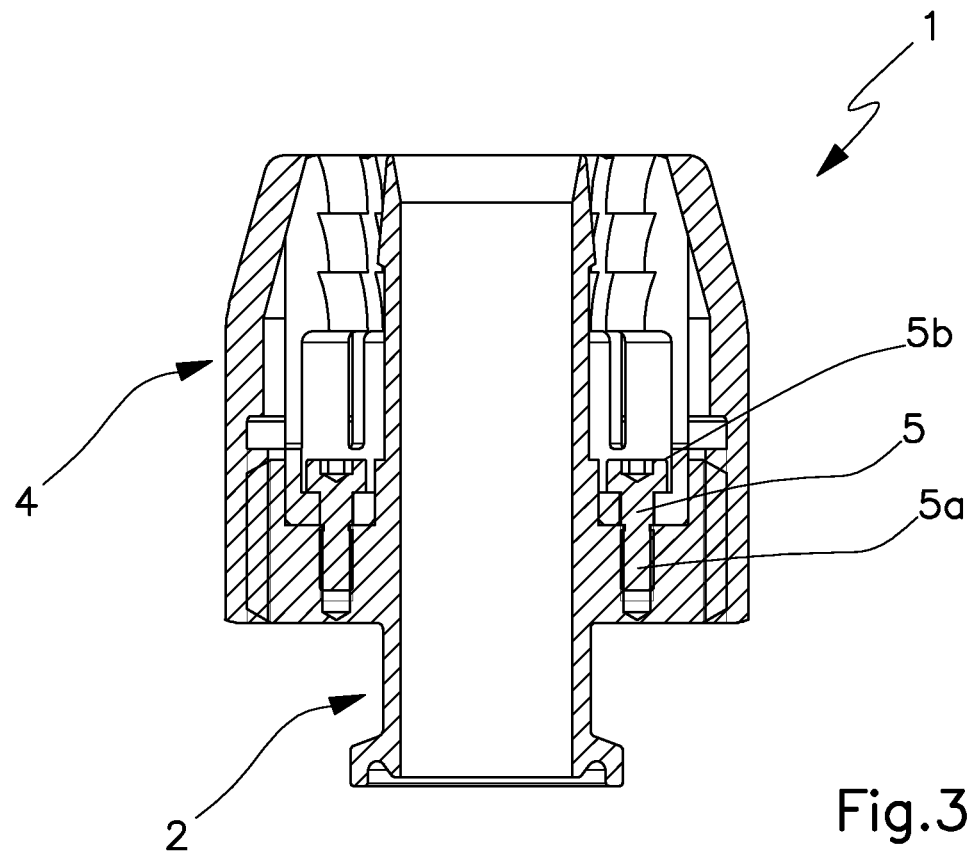
FIG. 3 shows a view in longitudinal cross-section according to the plane III-Ill shown in FIG. 2 of the same connector device.
Figure 2:
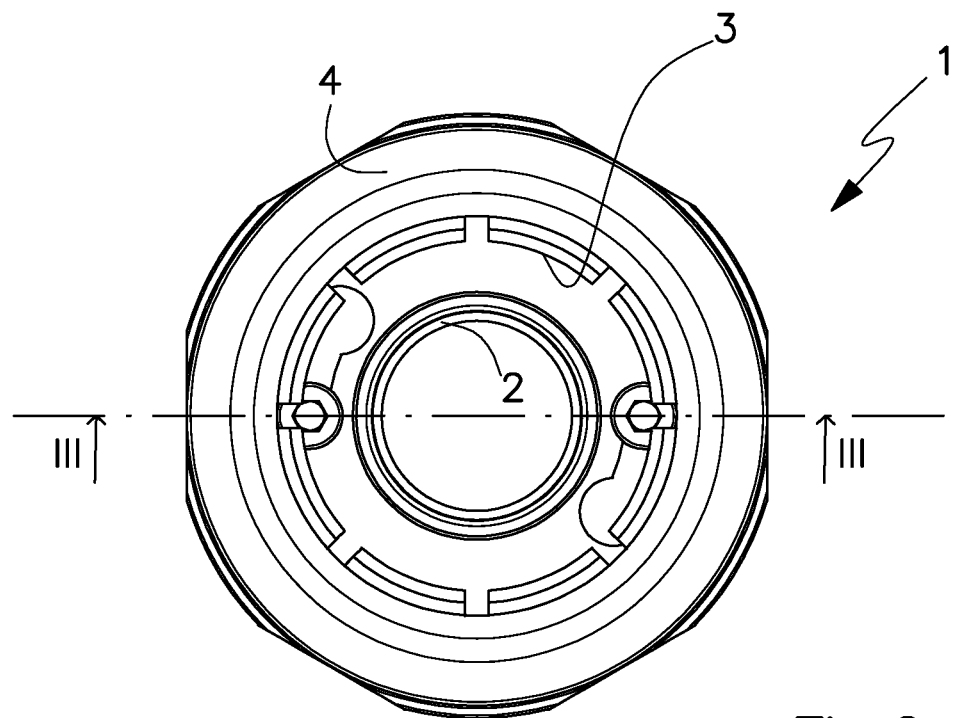
Figure 9:
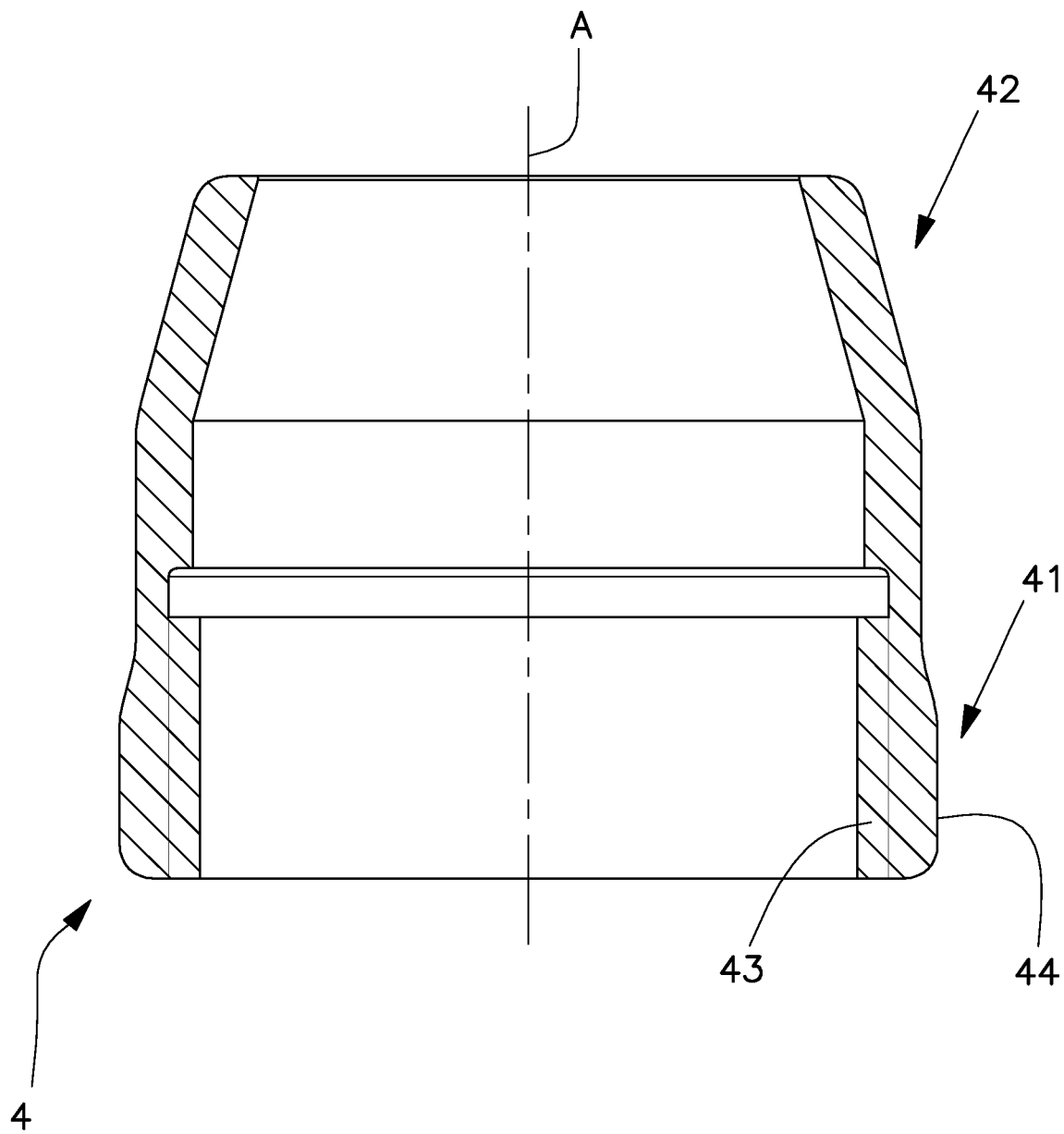
FIG. 9 shows a cross-sectional view according to a median longitudinal plane of a third component of the device according to the invention.

The operating portion 42 has a progressively decreasing diameter, in particular by assuming a conical shape, to engage, by compressing it on the flexible tube, the connecting end 32 of the clamping sleeve 3 (see FIGS. 3 and 9).

The functioning of the reusable sealing connector device for a flexible tube according to the invention is easy to understand from the foregoing description.

In a preparation step, the clamping sleeve 3 is locked to the tubular element 2, in the respective locking seat 25, by means of the locking elements 5.

The locking elements 5 can shape, as previously described, locking screws and be screwed into the locking holes 27 obtained in the clamping portion 23 of the tubular element 2.

Alternatively, the locking elements 5 can shape connections pins inserted through a forced coupling, with interference fit, in the same locking holes 27, which in this case are not threaded.

For greater safety, the heads 5b of the locking elements 5 can be locked by bayonet coupling in the shaped openings 35, 350, 351, obtained in the annular disc 33 of the clamping sleeve 3. Therefore, the sleeve 3 is rotated so that the head 5*b* of each locking element 5 already fixed to the locking seat 25 is inserted in the insertion portion 35*c*, 350*c*, 351*c*, rotated along the sliding portion 35*b*, 350*b*, 351*b* and finally locked at the fixing portion 35*a*, 350*a*, 351*a*, in particular thanks to the narrowed portion 35*d*, 350*d*, 351*d* which prevents accidental disengagement of the clamping sleeve 3 from the tubular element 2.

The clamping ferrule 4 is inserted around the flexible tube to be connected at a respective end.

Such end of the flexible tube, carrying the clamping ferrule 4 is inserted around the connecting portion 21 of the tubular element 2, inside the connecting end 32 of the clamping sleeve 3, already securely locked to the tubular element 2 at the locking seat 25.

Finally, the clamping ferrule 4 is clamped to the tubular element 2, by screwing, at the respective threaded coupling portion 43 by engagement on the outer clamping surface 44, preferably by manual clamping or by means of a suitable wrench tool.

The flexible tube is thus securely connected with the connector device 1.

To disassemble the clamping sleeve 3 from the tubular element 2 it is sufficient to rotate the same clamping sleeve 3 in a reverse direction with respect to what has been described above, with a reduced angular width, sufficient to bring the heads 5*b* of locking elements 5 to the insertion openings 35*c*, 350*c*, 351*c* so as to simply extract the sleeve 3 from the locking seat 25. The time required for this operation is very short, in the order of a fraction of a second.

The connector device according to the invention thus achieves the scope of providing a secure and at the same time easy connection both for the engagement and disengaging of a flexible tube.

Such scope is reached mainly thanks to the secure locking between the clamping sleeve 3 and the tubular element 2, preferably obtained through the locking elements 5 or, alternatively, through a forced coupling with interference fit, in a housing seat 25 provided on the tubular element 2 or through the help of fixing pins pushed into locking holes made on the same tubular element 2 and locked to the clamping sleeve 3.

However, only the clamping ferrule 4 cooperates with the clamping sleeve 3 by its respective operating portion 42, to clamp or disassemble the flexible tube, while the clamping sleeve 3 and the tubular element 2 are pre-assembled by a locking, in any case, stable but easily removable by the operator.

In practice, the used materials as well as the size and shape may vary according to the needs.

Should the technical characteristics mentioned in the claims be followed by reference signs, such reference signs were included for the sole purpose of increasing the understanding of the claims and thus they shall not be deemed limiting the scope of the element identified by such reference signs by way of example.

The invention claimed is:

1. A reusable sealing connector device for a flexible tube, the reusable sealing connector device comprising:
   a tubular element on which an end portion of said flexible tube is predisposed to be inserted along a longitudinal axis of said tubular element;
   a clamping sleeve predisposed to be inserted axially around said tubular element, said clamping sleeve comprising a connecting end divided into at least a pair of clamping segments predisposed to engage, in a flexible manner, an inserted portion of said flexible tube on said tubular element; and
   a clamping ferrule comprising an operating portion predisposed to be inserted around said clamping sleeve for compressing said clamping segments against said inserted portion of said flexible tube, said tubular element comprising an annular locking seat extending around said longitudinal axis, said tubular element being provided internally with at least one locking hole arranged parallel to said longitudinal axis, said clamping sleeve comprising an end locking portion configured to be inserted into said locking seat, said end locking portion comprising at least one opening configured to be aligned at least partially, in an assembled state, with said at least one locking hole, to lock said end locking portion of said clamping sleeve in an axial direction and a rotational direction about said longitudinal axis, inserted into said locking seat of said tubular element, by interposing at least one locking element inserted through said at least one opening and secured in said at least one locking hole.

2. A device according to claim 1, wherein said at least one locking hole is threaded, said at least one locking element being a screw.

3. A device according to claim 1, wherein said at least one locking element comprises a connecting pin, and said at least one locking hole is dimensioned for a force fit with said connecting pin.

4. A device according to claim 1, wherein said at least one opening is shaped so as to permit a bayonet locking.

5. A device according to claim 4, wherein said at least one opening comprises an insertion portion of transverse size for inserting a head of said at least one locking element, a sliding portion and a fixing portion having a transverse size substantially corresponding to a stem of said at least one locking element, and a narrowed portion interposed between said sliding portion and said fixing portion, said narrow portion having a reduced transverse size with respect to a transverse dimension of said stem of said at least one locking element, said sliding portion permitting a relative motion of said clamping sleeve with respect to said tubular element when said at least one locking element is fixed to said at least one locking hole and said stem slides along said sliding portion.

6. A device according to claim 5, wherein said sliding portion has a curved profile, to allow a relative rotation of said clamping sleeve with respect to said tubular element around said longitudinal axis, when said at least one locking element is fixed to said at least one locking hole and said locking portion of said clamping sleeve is inserted into said annular locking seat of said tubular element.

7. A device according to claim 5, wherein said narrowed portion of said at least one opening comprises at least one tooth protruding internally to said at least one opening for making a snap lock between said sleeve and said tubular element through interposition of said at least one locking element.

8. A device according to claim 7, wherein said narrowed portion of said at least one opening comprises another tooth to provide a pair of teeth protruding internally to said at least one opening and facing each other, to provide a snap lock between said sleeve and said tubular element.

9. A device according to claim 7, wherein said at least one opening has an open profile on a rim of said end locking portion.

10. A device according to claim 1, wherein said tubular element comprises at least another locking hole to provide at least two locking holes for respective locking elements and said end locking portion comprises at least another opening to provide at least a plurality of openings.

11. A device according to claim 1, wherein said at least one locking hole is defined on a bottom of said locking seat.

12. A device according to claim 11, wherein said bottom of said annular locking seat extends on a plane substantially orthogonal to said longitudinal axis in said assembled.

13. A device according to claim 1, wherein said tubular element so comprises a clamping portion, said clamping portion comprising an external threaded surface, said clamping ferrule comprising a coupling portion internally threaded for reciprocal clamping of said tubular element and said clamping ferrule by screwing.

14. A device according to claim 13, wherein said coupling portion of said clamping ferrule and said clamping portion of said tubular element comprise a thread of one of DIN 405 and DIN 20400, for reciprocal screwing.

15. A device according to claim 6, wherein said narrowed portion of said at least one opening comprises at least one tooth protruding internally to said at least one opening for making a snap lock between said sleeve and said tubular element through interposition of said at least one locking element.

16. A device according to claim 15, wherein said narrowed portion of said at least one opening comprises another tooth to provide a pair of teeth protruding internally to said at least one opening and facing each other, to provide a snap lock between said sleeve and said tubular element.

17. A device according to claim 15, wherein said at least one opening has an open profile on a rim of said end locking portion.

18. A device according to claim 1, wherein said tubular element comprises at least another locking hole and yet another locking hole to provide three locking holes for respective locking elements and said end locking portion comprises another opening and yet another opening to provide three openings.

* * * * *